US006567679B1

(12) United States Patent
Khuri et al.

(10) Patent No.: US 6,567,679 B1
(45) Date of Patent: May 20, 2003

(54) METHOD OF USING A PH TISSUE MONITOR

(75) Inventors: Shukri F. Khuri, Westwood, MA (US); Patrick Treanor, Dedham, MA (US)

(73) Assignee: E-Monitors, Inc., Tewksbury, MA (US)

( * ) Notice: Subject to any disclaimer, the term of this patent is extended or adjusted under 35 U.S.C. 154(b) by 0 days.

(21) Appl. No.: 09/339,081

(22) Filed: Jun. 23, 1999

Related U.S. Application Data

(60) Provisional application No. 60/136,502, filed on May 28, 1999.

(51) Int. Cl.[7] .................................................. A61B 5/00
(52) U.S. Cl. ........................... 600/345; 604/65; 604/66; 604/67; 126/897
(58) Field of Search ........................... 600/18, 345–350; 607/17–23; 604/65–67

(56) References Cited

U.S. PATENT DOCUMENTS

| | | | |
|---|---|---|---|
| 3,973,555 A | 8/1976 | Möller et al. .................. 128/2 |
| 4,252,124 A | 2/1981 | Maurer et al. ............... 128/635 |
| 4,413,628 A | 11/1983 | Tamulis ....................... 128/635 |
| 4,467,807 A | 8/1984 | Bornzin ....................... 128/419 |
| 4,717,548 A | 1/1988 | Lee .............................. 422/68 |
| 4,774,956 A | 10/1988 | Kruse et al. ................. 128/635 |
| 4,912,417 A | 3/1990 | Gibboney et al. ........... 324/438 |
| 5,024,668 A | * 6/1991 | Peters ........................... 600/18 |
| 5,051,352 A | 9/1991 | Martindale et al. ............ 435/1 |
| 5,063,930 A | 11/1991 | Nucci .......................... 128/632 |

(List continued on next page.)

FOREIGN PATENT DOCUMENTS

| | | |
|---|---|---|
| CA | 2151579 | 12/1995 |
| DE | 24 48 459 | 4/1975 |
| DE | 32 43 094 A1 | 5/1983 |
| EP | 0 354 719 A1 | 2/1990 |
| EP | 0 522 727 A1 | 1/1993 |
| FR | 2.198.638 | 9/1972 |
| FR | 2 744 804 | 8/1997 |
| GB | 2 045 940 | 11/1980 |
| JP | 08-182665 | 7/1996 |
| NL | 7415486 | 5/1976 |
| WO | WO 92/19150 | 11/1992 |
| WO | WO 98/26709 | 6/1998 |

OTHER PUBLICATIONS

Khuri, Shukri, F., et al., "The Significance of the Late Fall in Myocardial $Pco_2$ and Its Relationship to Myocardial pH after Regional Coronary Occlusion in the Dog," Circulation Research, 56:537–547 (1985).

Reifart, Nicholas, MD, et al., "Effects of Bepridil on Regional Myocardial Ischemia and Comparison with Verapamil," The American Journal of Cardiology, 58:541–546 (1986).

Lange, Rüdiger, M.D., et al., "Time Course of Ischemic Alternations and Hypothermic During Normothermic Arrest and Its Reflection by On–Line Monitoring of Tissue pH," Journal of Thoracic Cardiovascular Surgery, 86:418–434 (1983).

(List continued on next page.)

Primary Examiner—Robert L. Nasser
(74) Attorney, Agent, or Firm—Bowditch & Dewey, LLP

(57) ABSTRACT

The invention relates to the use of pH measurements of tissue as a system for controlling diagnostic and/or surgical procedures. The invention also relates to an apparatus used to perform tissue pH measurements. Tissue pH measurements can be used as a method to determine ischemic segments of the tissue and provide the user with courses of conduct during and after a surgical procedure. When ischemia is found to be present in a tissue, a user can effect an optimal delivery of preservation fluids to the site of interest and/or effect a change in the conduct of the procedure to raise the pH of the site.

32 Claims, 5 Drawing Sheets

U.S. PATENT DOCUMENTS

| | | | |
|---|---|---|---|
| 5,199,428 A | * 4/1993 | Obel et al. | 607/22 |
| 5,256,660 A | 10/1993 | Swan | 514/238.8 |
| 5,304,495 A | 4/1994 | Yim | 436/68 |
| 5,325,709 A | 7/1994 | Lee | 73/61.43 |
| 5,472,876 A | 12/1995 | Fahy | 435/284.1 |
| 5,522,389 A | 6/1996 | Fischer et al. | 128/634 |
| 5,533,971 A | 7/1996 | Phipps | 604/20 |
| 5,603,817 A | 2/1997 | Settler et al. | 204/433 |
| 5,753,207 A | 5/1998 | Zuo et al. | 424/9.36 |
| 5,766,432 A | * 6/1998 | Dunn et al. | 600/345 |
| 5,788,631 A | 8/1998 | Fiddian-Green | 600/309 |
| 5,813,403 A | * 9/1998 | Soller et al. | 600/322 |
| 6,040,046 A | 4/2000 | Hassanein | 435/284.1 |
| 6,090,096 A | * 7/2000 | St. Boar et al. | 600/18 |
| 6,100,082 A | 8/2000 | Hassanein | 435/284.1 |

OTHER PUBLICATIONS

Randolph, John D., M.D., et al., "Improved Myocardial Preservation With Oxygenated Cardioplegic Solutions as Reflected by On–Line Monitoring of Intramyocardial pH During Arrest," Journal of Vascular Surgery, 3:216–225 (1986).

Khuri, Shukri F., M.D., et al., "First Report of Intramyocardial pH in Man: I. Methodology and Initial Results," Medical Instrumentation, 18:167–171 (1984).

Khuri, Shukri F., M.D., and Marston, William A. B.Sc., "On–Line Metabolic Monitoring of the Heart During Cardiac Surgery," Symposium on the Latest Advances in Cardiac Surgery, pp. 439–453, No date given.

Khuri, Shukri F., and Warner, Kenneth G., "Intraoperative pH Monitoring for the Detection of Progressive Myocardial Ischemia," Myocardial Protection in Cardiac Surgery, Brockton/West Roxbury Veterans Administration Medical Center–Harvard Medical School, West Roxbury, MA, pp. 399–412 (1987).

Khuri, Shukri F., MD, "Myocardial Protection During Reoperative Valve Surgery," A Textbook of Cardioplegia for Difficult Clinical Problems, 21:221–235 (1992).

Hassanein, W., et al., "Continuous Perfusion of Donor Hearts in the Beating State Extends Preservation Time and Improves Recovery of Function," *The Journal of Thoracic and Cardiovascular Surgery*, 116:821–830 (1998) XP002929772.

Khuri, Shukri F., et al., "Changes in Intramyocardial ST Segment Voltage and Gas Tensions with Regional Myocardial Ischemia in the Dog," Circulation Research, 37:455–463 (1975).

Khuri, Shukri F., et al., "Intramural $Pco_2$: a reliable index of the severity of myocardial ischemic injury," American Journal Physiol., 237(2) :H253–H259 (1979).

Alam, S., et al., "Lack of Effect of Nitroglycerin on the Transmural Variation of Tissue pH During Fixed Coronary Stenosis," Z. Kardiol., 72, 000–000 (1983).

Siouffi, Samer Y., et al., "Methods for the Metabolic Quantification of Regional Myocardial Ischemia," Journal of Surgical Research, 43:360–378 (1987).

Warner, Kenneth G., et al., "Significance of the Transmural Diminution in Regional Hydrogen Ion Production After Repeated Coronary Artery Occlusions," Circulation Research, 64:616–628 (1989).

Khuri, Shukri F., et al., "Metabolic Correlates of Myocardial Stunning and the Effect of Cardiopulmonary Bypass," Journal of Cardiac Surgery, 8:262–270 (1993).

Khabbaz, Kamal R., et al., "Simultaneous In Vivo Measurements of Intracellular and Extracellular Myocardial pH During Repeated Episodes of Ischemia," Current Surgery, 46:399–400 (1989).

Axford, Trevor C., et al., "Electrod–derived myocardial pH measurements reflected intracellular myocardial metabolism assessed by phosphorus 31 —nuclear magnetic resonance spectroscopy during normothermic ischemia," Journal of Thoracic and Cardiovascular Surgery, 103:902–907 (1992).

Zankoul, Fuad E., et al., "Time Course and Significance of Myocardial Tissue Acidosis During Global Ischemia and Sanguineous Reperfusion in the Isolated Rabbit Heart," Surgical Forum, 48:353–355 (1997).

Lange, Ruediger, et al., "Intramyocardial pH Measurement: A Useful Tool for the On–Line Assessment of Ischemic Damage and the Adequacy of Myocardial Preservation During Open Hear Surgery?," American College of Surgeons, Surgical Forum 33:290–292 (1982).

Lange, Rüdiger, et al., "The relative importance of alkalinity, temperature, and the washout effect of bicarbonate–buffered, multidose cardioplegic solution," Myocardial Protection, 70:I–75–I–83 (1984).

Khuri, Shukri F., et al., "The superiority of Continuous Cold Blood Cardioplegia in the Metabolic Protection of the Hypertrophied Human Heart," Journal of Thoracic and Cardiovascular Surgery, 95:442–454 (1998).

Warner, Kenneth G., et al., "Reduction in Myocardial Acidosis Using Blood Cardioplegia," Journal of Surgical Research, 45:247–256 (1987).

Warner, Kenneth G., et al., "Regional Changes in Myocardial Acid Production during Ischemic Arrest: A Comparison of Sanguineous and Asanguineous Cardioplegia," Annals of Thoracic Surgery, 45:75–81 (1988).

Dearani, Joseph A., et al., "Myocardial pH and Coronary Perfusion Pressure as Indicators of Survival During Cardiopulmonary Resuscitation," American College of Surgeons, Surgical Forum, 40:46–48 (1989).

Martin, David, et al., "The Effects of Normothermic and Hypothermic Cardiopulmonary Bypass on Defibrillation Energy Requirements and Transmyocardial Impedance," Journal of Thoracic and Cardiovascular Surgery, 109:981–988 (1995).

Khuri, Shukri F., et al., "First report of intramyocardial pH in man," Journal of Thoracic and Cardiovascular Surgery, 86:667–678 (1983).

Khuri, Shukri F., et al., "Observations on 100 patients with continuous intraoperative monitoring of intramyocardial pH," Journal of Thoracic and Cardiovascular Surgery, 89:170–182 (1985).

Khuri, Shukri F., et al., "Intraoperative assessment of the physiologic significance of coronary stenosis in humans," Journal of Thoracic and Cardiovascular Surgery, 92:79–87 (1986).

Khuri, Shukri F., "Myocardial Preservation During Coronary Artery Bypass Surgery," Cardiac Surgery: State of the Art Reviews, 1:59–75 (1986).

Warner, Kenneth G., et al., "Metabolic and Microscopic Evidence of Ischemia in Valvular Heart Operation: Are we Really Protecting the Hypertrophied Ventricle?," American College of Surgeons, Surgical Forum, 36:216–218 (1985).

Warner, Kenneth G., et al., "Structural and Metabolic correlates of cell injury in the hypertrophied myocardium during valve–replacement," Journal of Thoracic and Cardiovascular Surgery, 93:741–754 (1987).

Josa, Miguel, et al., "The Superiority of Blood Over Crystalloid Cardioplegia in Preventing Myocardial Acidosis During Global Cardiac Arrest," Cardiac Surgery, Surgical Forum, 253–255.

Dearani, Joseph A., et al., "Routine Measurement of Myocardial Temperature is Not Reflective of Myocardial Metabolism During Cardiac Surgery," American College of Surgeons, Surgical Forum, 41:228–230 (1990).

Khuri, Shukri F., et al., "Intraoperative Assessment of the Stunned versus Infarcted Myocardium with the Simultaneous Use of Transesophageal Echocardiography and the Measurement of Myocardial pH: Two Case Studies," Journal of Cardiac Surgery, 9:403–409 (1994).

Tantillo, Michael B., and Khuri, Shukri F., "Myocardial tissue pH in the assessment of the extent of myocardial ischemia and the adequacy of myocardial protection," Ischemia–reperfusion in cardiac surgery, 335–352 (1993).

Warner, Kenneth G., et al., "Comparative Response of Muscle and Subcutaneous Tissue pH During Arterial and Venous Occlusion in Musculocutaneous Flaps," Annals of Plastic Surgery, 22:108–116 (1989).

Kwasnik, Edward M., et al., "Hemodynamic and metabolic responses to graded microvascular occlusion," Journal of Vascular Surgery, 13:867–874 (1991).

Khuri, Shukri F., "Invited letter concerning: Changes in myocardial high–energy stores and carbohydrate metabolism during intermittent aortic crossclamping in dogs on cardiopulmonary bypass at 34° and 25° C," The Journal of Thoracic and Cardiovascular Surgery, 101:559–561 (1991).

* cited by examiner

METHOD OF USING A PH TISSUE MONITOR

RELATED APPLICATION

This application claims the benefit of U.S. Provisional Application No. 60/136,502, filed on May 28, 1999, the entire teachings of which are incorporated herein by reference.

BACKGROUND OF THE INVENTION

It is well known in the art to determine the pH in body fluids by using an electrode cell assembly and immersing the measuring electrode into a sample of the bodily fluid. The pH is known to be the symbol for the negative logarithm of the $H^+$ ion concentration. The pH value of the blood makes it possible to estimate the carbon dioxide level of the blood, for example. The increased carbon dioxide concentration in the blood indicates that the organs of the body are not being provided with enough oxygen, which can ultimately prove harmful.

It is also known in the art to measure tissue pH in myocardial tissue. Measurement of pH in myocardial tissue has been used to determine the presence of myocardial ischemia, as indicated by a decrease in pH. During cardiac surgery, the aorta is cross clamped and the myocardium is deprived of its blood and nutrient supply. To avoid potential damage to the heart, the pH of the myocardium can be monitored to determine tissue acidosis and thus the onset of myocardial ischemia.

There is an ongoing need, however, for further improvements in methods for diagnosing and treating ishemic tissue.

SUMMARY OF THE INVENTION

While ischemia or tissue acidosis, in cardiac tissue has been measured, methods to prevent and/or reverse cardiac acidosis were unknown. Surgeons did not know how to reverse tissue acidosis once discovered. The present invention relates to a method of using tissue pH measurements to diagnose ischemia and/or gauge the conduct of an operation by determining whether a site is ischemic. The current invention also provides methods by which tissue acidosis can be corrected once discovered.

The present invention relates to pH-guided management of tissue ischemia or the use of pH measurements of tissue as a system for controlling diagnostic and/or surgical procedures. A preferred embodiment of the invention relates specifically to an apparatus and method which is applicable to patients undergoing cardiac surgery. It employs a tissue electrode and monitor and comprises a series of steps that in a preferred embodiment are aimed at achieving a homogeneous distribution of cardioplegic solution during aortic clamping, and at insuring adequate revascularization of ischemic segments of the myocardium. The method using pH-guided myocardial management guides the conduct of operations, prevents damage to the heart, extends the safe period of oxygen deprivation, and improves the outcome of patients undergoing heart surgery.

The use of the pH-guided myocardial management method to identify ischemic segments of a myocardium can provide a user with options for specific courses of conduct, both during and after, the surgical procedure. These options include: effecting an optimal delivery of preservation solutions to the heart to reduce ischemia, assessing the adequacy of coronary revascularization following a heart surgery procedure, identifying viable but nonfunctioning heart muscle, prompting changes in the conduct of the surgical procedure, monitoring the pH of the heart muscle postoperatively and evaluating the efficacy of newer myocardial protective agents.

There are several methods of delivery of a pH electrode, used in pH-guided myocardial management, to a site of interest. The electrode can be delivered manually by the user. The electrode can also be delivered by a catheter through a percutaneous incision. The electrode can also be delivered by an endoscope, a colonscope or a laparoscope to a site of interest. Thus, in a preferred embodiment of the invention, the method can be applied to other tissue measurements such as brain tissue, kidney tissue, musculocutaneaus flaps or the small or large intestines. In another embodiment, the pH of transplanted organs, such as liver or kidney, can be measured to assist in the diagnosis and/or treatment of rejection since acidosis is an early sign of rejection.

Other methods can also be used to measure pH, including, in certain applications, surface pH measurements, magnetic resonance measurements, or optical methods using fiber optic probes.

When a user has found that tissue acidosis is present at a site of interest, the user can effect an optimal delivery of preservation fluids, or cardioplegia fluids, to the heart to raise the pH of the site. Several methods of providing optimal delivery of the cardioplegia solutions to the site are available to the user. These methods include: altering the flow rate of the preservation fluid, altering the temperature of the fluid, altering the site of delivery, repositioning the tip of the catheter, selectively directing the preservation fluid through the manifold, applying direct coronary artery pressure on the proximal portion of the artery, occluding the left main coronary artery with a balloon catheter, inflating the balloon of a retrograde coronary sinus catheter, administering a bolus of cardioplegia through the orifice of a right coronary artery and accelerating a surgical procedure.

When a user has found that tissue acidosis is present at a site of interest, the user can also prompt changes to the conduct of the surgical procedure to raise the pH of the site. Several methods of changing the surgical procedure are available to the user. These methods include: determining the need for revascularization of a specific segment of the myocardium, changing the order of revascularization, providing for additional revascularization, changing the operation or the surgeon to reduce ischemic time, canceling an operation and delaying the weaning of a patient from cardiopulmonary bypass.

The pH electrode itself can have a cable connected to a silver wire where the silver wire is an Ag/AgCl (silver/silver chloride) wire. The cable and wires are encased in a housing which is encased in shrink tubing. The electrode has a glass stem which houses the silver wire, a thermistor, a pH sensor, and a gelled electrolyte. The electrode has a bendable joint which allows the user to adjust the positioning of the electrode prior to or during use and which facilitates electrode removal after chronic insertion. The glass stem is pointed to allow direct insertion into tissues. In a preferred embodiment, the glass stem is made of lead glass.

Figure 1:
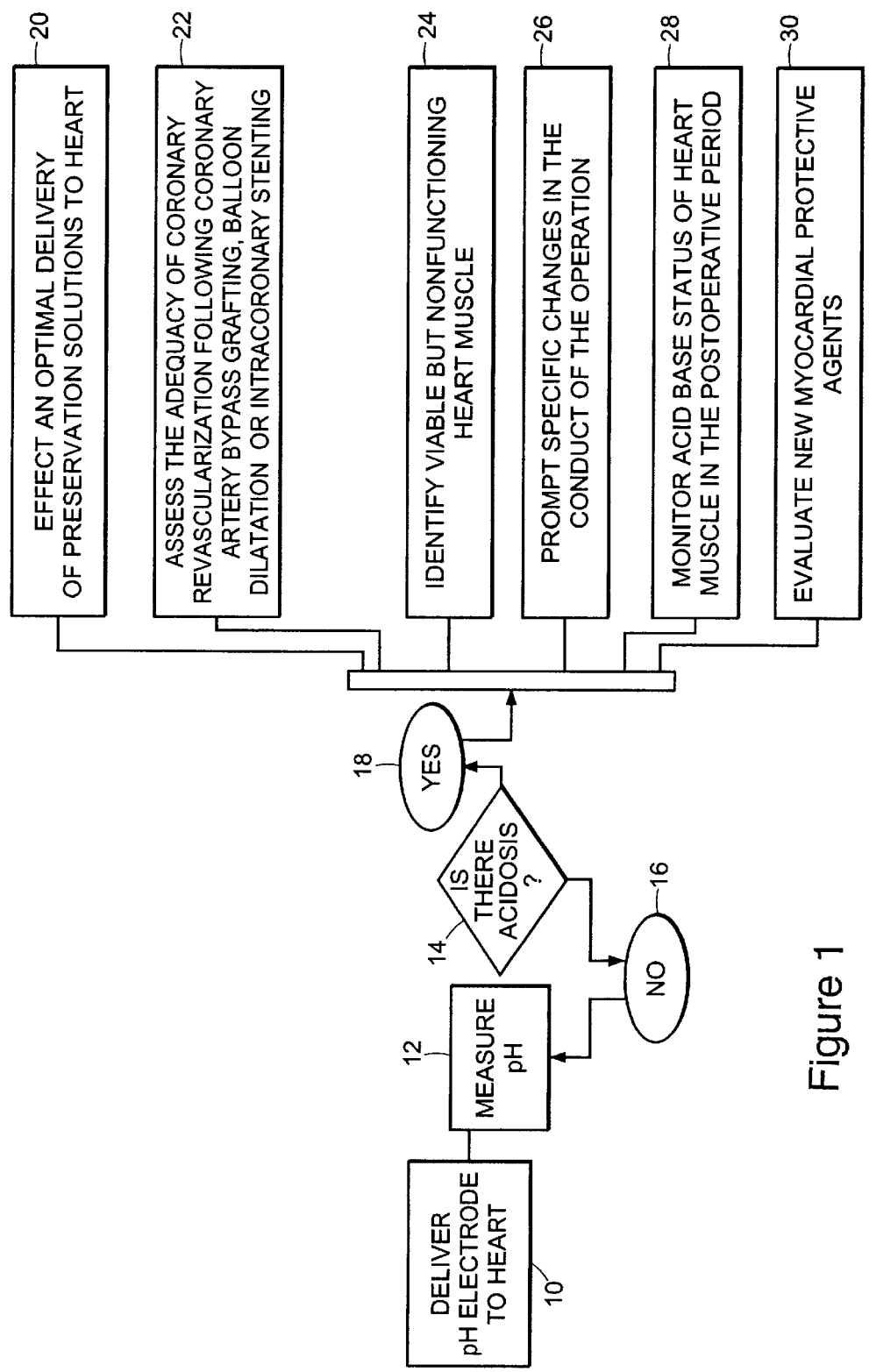
FIG. 1 illustrates a method of using tissue pH to identify ischemic segments of a myocardium and the options available to a user to utilize this information and take an appropriate course of action in accordance with a preferred embodiment of the present invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

FIG. 1 illustrates a method of using tissue pH to identify ischemic segments of the heart, which are regions of the heart muscle that are not receiving an adequate blood and nutrient supply, and the options available to a user to take advantage of this information and pursue an appropriate course of action. A user would first deliver a pH electrode to a patient's heart 10. The user would then measure the tissue pH as displayed on a monitor 12 and determine whether or not there was acidosis present in the tissue 14. If there is no tissue acidosis 16, the pH would be again measured 12. In a preferred embodiment, the pH is continually measured by the electrode with the pH measurements displayed on a monitor. If acidosis existed in the tissue 18, however, the user could use this information to take appropriate action such as, but not limited to, the following:

A user can effect an optimal delivery of the preservation solutions to the heart through one or more of a compendium of specific interventions 20. To perform open heart surgery, the aorta has to be clamped thus depriving the heart muscle from its blood, nutrient, and oxygen supply. A preservation solution, often referred to as a cardioplegic solution, is normally perfused into the heart and its blood vessels to prevent time-dependent ischemic damage. It has been shown that the measurement of tissue pH, which reflects, in part, the washout of the hydrogen ion generated by the metabolic processes, is a good indicator of the regional distribution of the preservation solution. It has also been shown this distribution to be markedly heterogenous and unpredictable, with segments of the myocardial wall suffering from acidosis because of failure of the cardioplegic solution to reach these segments. The main objective of pH-guided myocardial management is to prevent tissue acidosis in all the segments of the myocardium throughout the course of open heart surgery. This is achieved by insuring an adequate and a homogeneous delivery of the cardioplegic solution and an adequate revascularization of ischemic segments of the heart. These are achieved by maintenance of the myocardial pH as near normal as possible, with normal pH ranging between 7.2 and 7.4.

A user can also assess the adequacy of coronary revascularization following coronary artery bypass grafting, balloon dilatation or intracoronary stenting 22. This functionality employs the rate of washout of the hydrogen ion accumulating in the tissues during ischemia as an indication of the magnitude of tissue blood flow. Following restoration of flow through a newly constructed aorto-coronary bypass graft, no change in the pH of a myocardial segment subtended by that graft indicates inadequate revascularization. On the other hand, a rise in the pH of more than 0.1 pH units indicates restoration of effective tissue flow to the ischemic myocardium.

A user can also identify viable but non-functioning heart muscle 24, known as hibernating myocardium, which would improve its function with adequate coronary revascularization. pH-guided myocardial management has demonstrated that the ability of the non-contractile myocardial wall segment to produce acid, i.e. to exhibit tissue acidosis, is an indication of the viability and reversibility of dysfunction in this segment. Hence the procedure provides a tool with which the viability of the non-contractile myocardial segment can be assessed.

A user can also prompt specific changes in the conduct of the operation 26 after obtaining information regarding tissue pH. These changes in operating procedure are outlined in greater detail in FIG. 4.

A user can also monitor the acid-base status of the heart muscle in the post-operative period 28 and identify impending problems. This functionality allows the depiction of ischemic events in the intensive care unit within the first 72 hours postoperatively. This methodology is capable of continuous monitoring of regional issue metabolism and acid base balance in a patient, post-surgery. A fall in the myocardial pH of more than 0.1 pH units in the face of a stable blood pH is indicative of myocardial ischemia. The more severe the fall in the pH the more the magnitude of the ischemic insult. This functionality is achieved by implanting the electrodes in the myocardium in the usual way at the time of the operation and exteriorizing them through a special chest tube. The electrodes are pulled out in the surgical intensive care unit (SICU) after the monitoring is terminated by simply pulling on them along with the chest tube which houses them.

The user can also evaluate the efficacy of newer myocardial protective agents and methods in the prevention of tissue acidosis and the improvement of patient outcomes 30. To improve myocardial protection, a number of agents are being proposed as additions the cardioplegic solution, and new modalities for the administration of cardioplegia are being sought. pH-guided myocardial management provides a metabolic marker which can enable the assessment of the efficacy of these new agents and modalities in improving the degree of intraoperative protection, the hallmark of which can be the degree of prevention of acidosis during the period of aortic clamping. The variable employed to compare these methods of myocardial protection is the integrated mean myocardial pH during the period of aortic clamping. The higher the integrated mean pH during this period, the better is the degree of myocardial protection.

Figure 2:
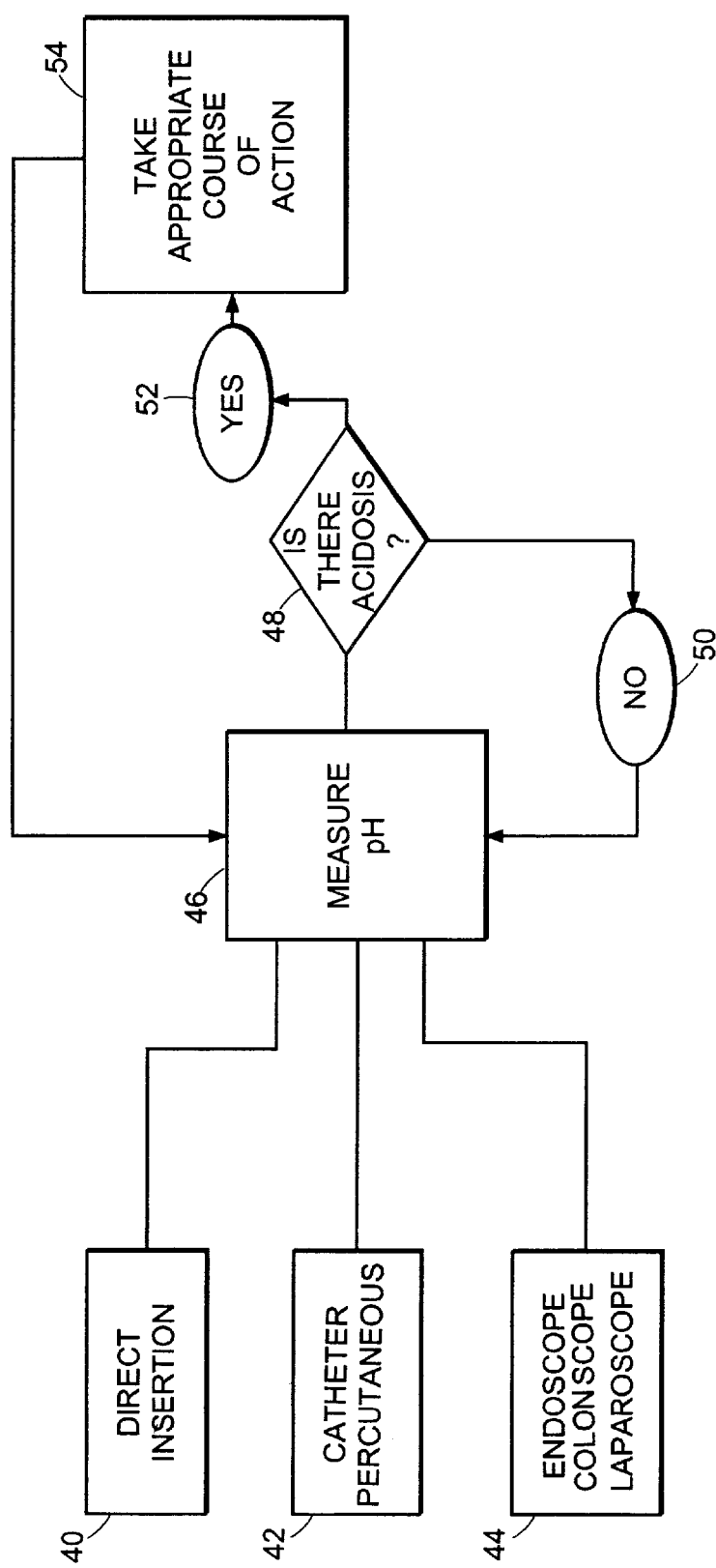
FIG. 2 illustrates the methods of delivery of a pH electrode to cardiac tissue in accordance with preferred embodiments of the present invention.

FIG. 2 illustrates various methods of delivery of a pH electrode to cardiac tissue. A user can implant the pH electrode using direct insertion 40. This can include opening the chest cavity of a patient during a cardiac surgery procedure and placing the electrode into the patient's cardiac tissue by hand. The user can also insert the pH electrode by means of a catheter using a percutaneous incision 42. A user can also insert the pH electrode by using an endoscope, colonscope or laparoscope 44. The user can then measure the pH of the tissue 46 and determine whether there is acidosis in the tissue 48. If no acidosis is found 50, the pH of the tissue can again be measured 46. If acidosis is found in the tissue 52, the user can then take an appropriate course of action 54, as outlined in FIG. 1.

Figure 3:
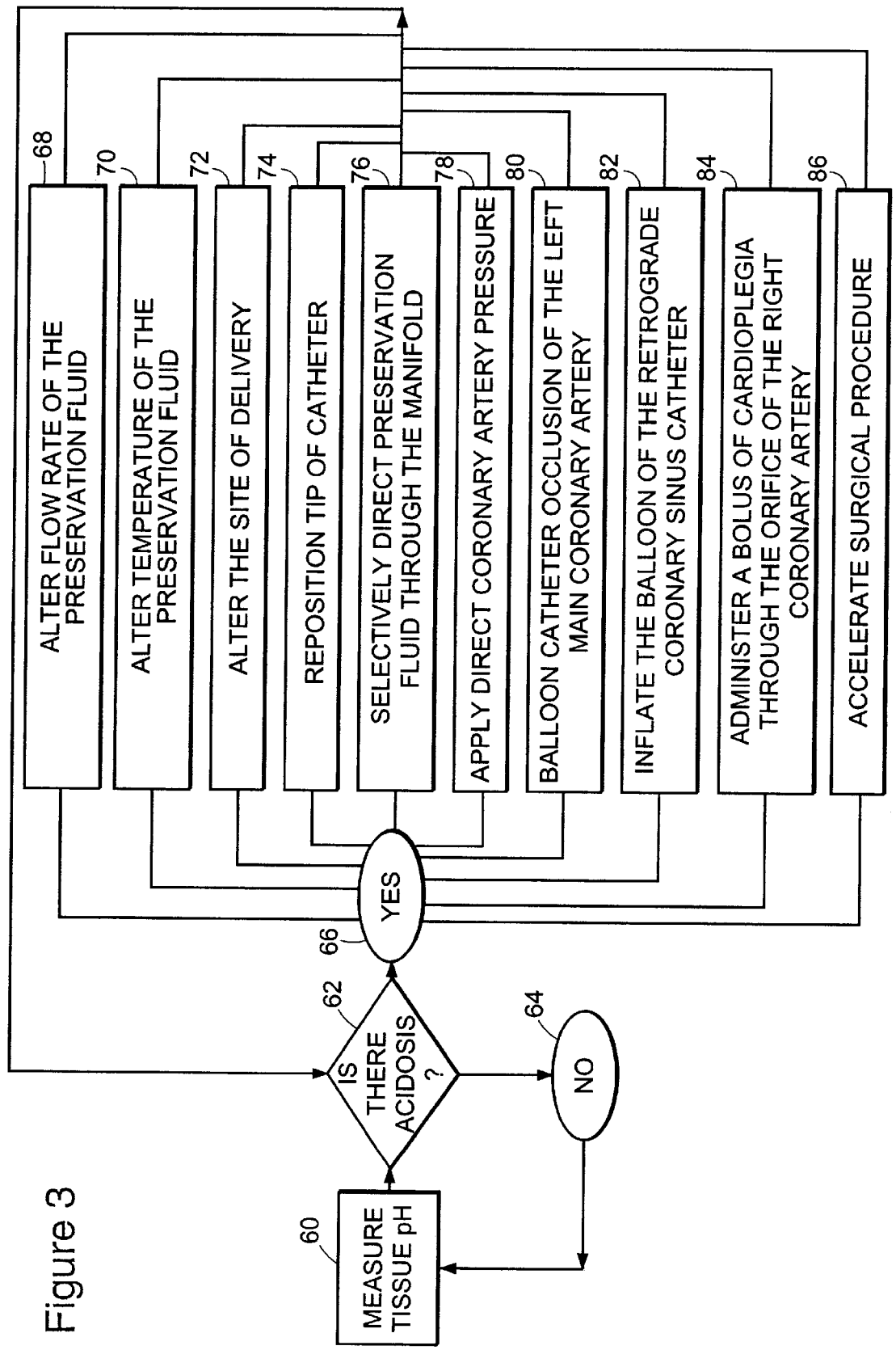
FIG. 3 illustrates a method of effecting an optimal delivery of preservation solution to the heart during surgery in accordance with a preferred embodiment of the present invention.

FIG. 3 illustrates a method of providing for an optimal delivery of preservation solution to a heart during surgery. In this method, a user can first measure cardiac tissue pH 60 and determine whether there is acidosis in the tissue 62. If no acidosis is found 64, the pH of the tissue can again be measured 62. In a preferred embodiment, the pH is continuously measured and monitored. If acidosis is found in the tissue 66, the user can then effect an optimal delivery of the preservation solutions to the heart through one or more of a compendium of specific interventions. Interventions to be used to effect an adequate and a homogeneous delivery of the cardioplegic solution include, but are not limited to, the following maneuvers:

The user can alter the flow rate of the preservation solution 68 to provide an optimal delivery of the cardioplegia solution. The perfusionist controls the flow rate of the cardioplegic solution administered. pH-guided myocardial management has demonstrated that patients and myocardial segments differ in the flow rate necessary to prevent acidosis. Therefore, changing the flow rate of the cardioplegia solution can alter and improve tissue pH.

The user can also alter the temperature of the preservation solution 70 to optimize solution delivery. Changes in myocardial temperature, which can range widely in the course of cardiac surgery, effect various degrees of vasoconstriction and vasodilatation of the coronary vasculature. This, in turn, will effect the distribution of the cardioplegic solution and also the level of tissue acidosis. Avoidance of tissue acidosis can be achieved either by cooling or by re-warming the cardioplegic solution, depending on the effect of temperature on the regional distribution of the cardioplegic solution. pH-guided myocardial management has demonstrated that the effect of temperature on the regional distribution of the cardioplegic solution is totally unpredictable and, hence, continuous monitoring of myocardial tissue pH allows the determination of the myocardial temperature which is most likely to prevent myocardial acidosis. Opposite effects on myocardial pH have been observed from patient to patient with both cooling and rewarming. In general, however, giving warm cardioplegia effected an improvement in tissue pH in most patients.

To provide an optimal delivery of the solution, the user can also alter the site of delivery of the cardioplegic solution 72. The cardioplegic solution can be delivered through several sites: antegrade through the aortic root, antegrade through the orifice of the right and/or left main coronary arteries, antegrade through the proximal ends of newly constructed grafts, and retrograde through the coronary sinus. pH-guided myocardial management allows the surgeon to choose the site or combination of sites of administration which can best avoid regional acidosis.

The user can reposition the tip of the catheter through which the cardioplegic solution is delivered 74 to optimize delivery. This may need to be performed in patients with a very short left main coronary artery when cardioplegia is administered through the orifice of the left main. It can also be useful in pulling back on a retrograde catheter which is pushed too far into the coronary sinus.

The user can also selectively direct the cardioplegic solution through a manifold so as to reduce the steal of the solution 76. The cardioplegic solution can be delivered through a manifold having several catheters radiating from a single source. This arrangement of the manifold is known as a "turkey foot". When the cardioplegic solution is administered through more than one of these catheters simultaneously, there is a marked heterogeneity in the distribution of the solution to the various myocardial segments supplied by these catheters. The solution often moves preferentially into the catheter supplying the myocardial segment with least resistance, usually the myocardial segment with least coronary artery disease. This is what is referred to as a "steal phenomenon." Monitoring myocardial pH, which capitalizes on the fact that the rate of washout of the hydrogen ion in tissue is indicative of the magnitude of tissue flow, can determine which segments of the myocardium are receiving the cardioplegic solution and which segments are deprived of cardioplegia because of the steal phenomenon. When steal is encountered, homogeneity of the distribution of the cardioplegic solution can be achieved by occluding the catheters responsible for the steal and by specifically directing the flow only into the areas exhibiting acidosis.

The user can also apply direct coronary artery pressure on the proximal portion of the artery to distally direct cardioplegia flow through a newly constructed graft 78. This pressure can force the cardioplegia solution to an area with low pH, to lower tissue acidosis in that area.

The user can perform a balloon catheter occlusion of the orifice of the left main coronary artery during the delivery of retrograde cardioplegia through the coronary sinus or through the proximal ends of recently constructed saphenous vein grafts 80. The balloon catheter occlusion of the left main coronary artery prevents the steal phenomenon, where the solution follows the path of least resistance, and forces the cardioplegia solution to an area of low pH. This process can reverse acidosis of an area showing a low pH.

The user can also inflate the balloon of a retrograde coronary sinus catheter while the cardioplegic solution is being administered antegrade 82. Normally, if cardioplegia is being delivered antegrade and retrograde simultaneously, the balloon in the coronary sinus is kept deflated. A more homogeneous distribution of the cardioplegic solution can be achieved if the balloon in the coronary sinus is kept inflated while the cardioplegia is delivered simultaneously antegrade and retrograde.

The user can also administer a bolus of cardioplegia through the orifice of the right coronary artery when the latter is a dominant, non-obstructed vessel 84. In the course of an open heart operation in which the aortic root is open, cardioplegia can be administered through the orifice of the right coronary artery in addition to the orifice of the left coronary artery. This, however, can be tedious and time consuming, hence it is not a common practice. pH-guided myocardial management has shown that the posterior left ventricular wall is more vulnerable to refractory myocardial acidosis if the right coronary artery is dominant and no cardioplegia is administered through it. Hence, if in the course of pH-guided myocardial management, refractory acidosis is encountered in the posterior wall, administering a bolus of cardioplegia through the orifice of the right coronary artery, if the latter is dominant, can insure adequate delivery of the cardioplegic solution to the posterior wall and can reverse the acidosis.

A user can also accelerate the surgical procedure 86 when tissue acidosis is present. By monitoring tissue acidosis, a user can avoid either using his time wastefully or attempting nonstandard or potentially ineffectual surgical procedures. Also, in few patients, less than 5%, there is no known method to prevent tissue acidosis and the surgical procedure must be accelerated. With the acceleration of a procedure, the aorta, which is clamped during the surgery, is unclamped sooner than planned, thus allowing oxygen rich blood to reach the heart muscle, thereby reversing acidosis.

In the event that one of the described options, 68 through 86, fails to relieve the ischemic condition, as evidenced by the display of tissue pH levels on the pH monitor, the user can use any of the other described options to attempt to raise tissue pH.

Figure 4:
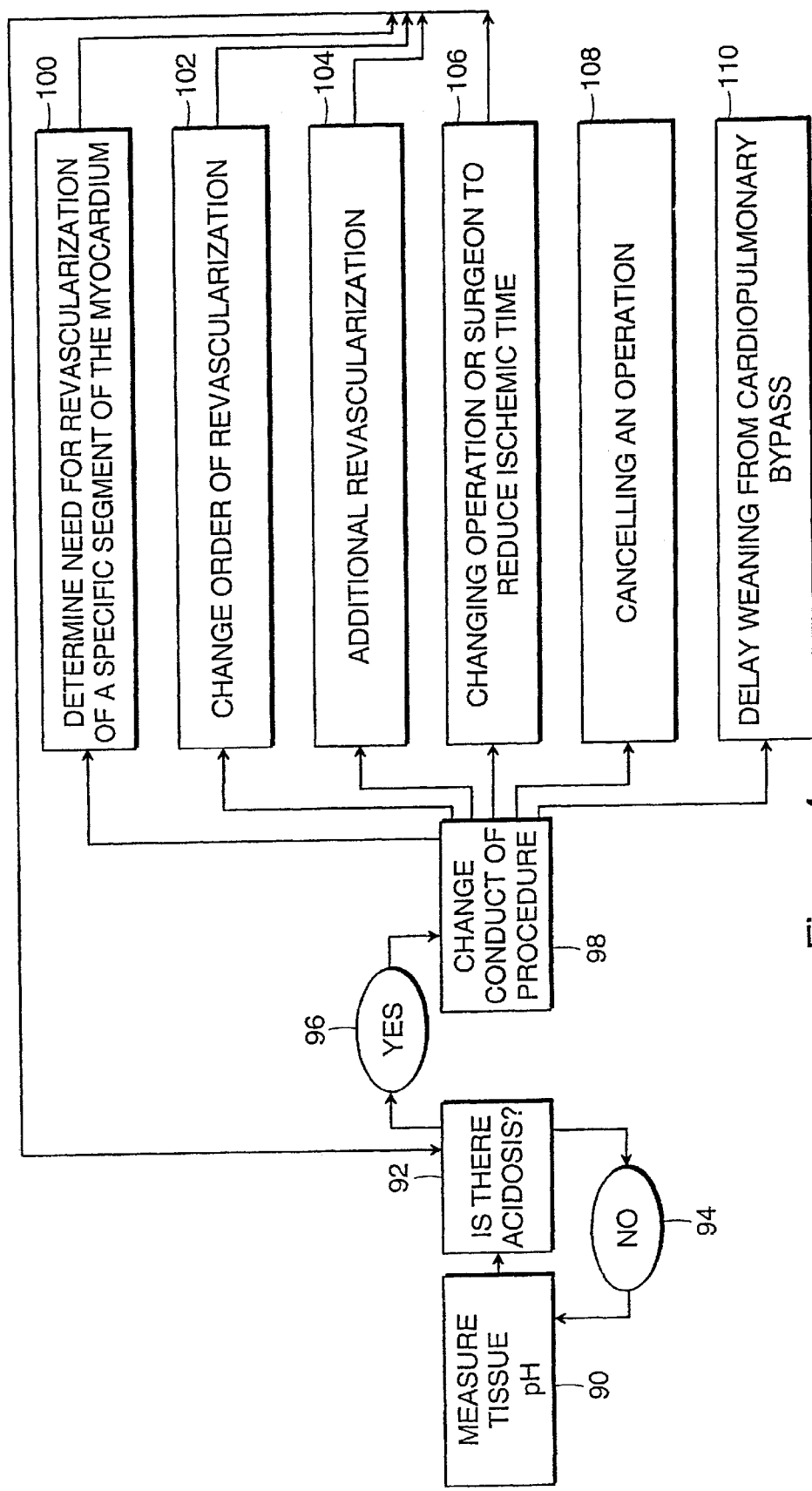
FIG. 4 illustrates a method of using the pH electrode to measure the condition of tissue and alter the conduct of an operation involving the tissue in accordance with a preferred embodiment of the present invention.

FIG. 4 illustrates a method of using the pH electrode to prompt specific changes in the conduct of an operation after determining there is tissue acidosis. In this method, a user first measures cardiac tissue pH 90 and determines whether there is acidosis in the tissue 92. If no acidosis is found 94, the pH of the tissue can again be continuously or periodically measured 90. If acidosis is found in the tissue 96, the user can then change the conduct of the procedure 98.

These changes can include, but are not limited to the following maneuvers. First, the determination of the need for the revascularization of a specific segment of myocardium 100. The ability to identify which specifically are the segments of the myocardium that need revascularization can be lifesaving. Segments requiring revascularization can be determined by either examining the onset of regional acidosis in the course of an operation or the response of the myocardial pH to atrial pacing. The response to atrial pacing can be utilized intra-operatively, postoperatively in the SICU, and in the cardiac catheterization laboratory.

The user can also change the order of revascularization. pH-guided myocardial management allows the surgeon to revascularize the most ischemic segments of the myocardium first so as to minimize the degree of acidosis encountered in the course of aortic clamping.

The user can also change the procedure by providing additional revascularization of the heart 104. pH-guided myocardial management involves identifying ischemic segments of the left ventricular wall that require revascularization, often unplanned preoperatively.

The user can also change the operation or the surgeon to reduce the duration of the ischemic time 106. pH-guided myocardial management allows for reductions in the magnitude of the planned operation in several ways. When pH monitoring depicts a significant amount of myocardial acidosis which cannot be corrected, the need to reduce the ischemic time becomes more important than the potential benefits of certain parts of the operation that can be dispensed with, such as the construction of an additional graft. pH monitoring also allows the surgeon to abandon a planned part of the operation because it uncovers no real need for this part. In this context, pH-guided myocardial management also plays a major value in the teaching of residents because it provides the attending surgeon with the information on what parts of the operation he/she can give to the resident, and what part the attending surgeon should be doing himself/ herself, since residents, particularly early in their training, can be fairly tardy in performing these operations.

The user can also cancel an operation 108 if, based on the pH measurements, the risk of the procedure is found to exceed the benefit.

Lastly, the user can delay the weaning from cardiopulmonary bypass until the oxygen debt, represented by residual acidosis during reperfusion, is fully paid 110. Weaning from cardiopulmonary bypass in the presence of myocardial acidosis may cause the hemodynamics to deteriorate postoperatively, often prompting the re-institution of cardiopulmonary bypass. When the heart is subjected to significant ischemia during the period of aortic clamping or reperfusion, a significant amount of time may be needed until the ischemia reverses to normal levels.

In the event that one of the described options, 100 through 106, fails to relieve the ischemic condition, as evidenced by the display of tissue pH levels on the pH monitor, the user can use any of these other described options to attempt to raise tissue pH.

Figure 5:
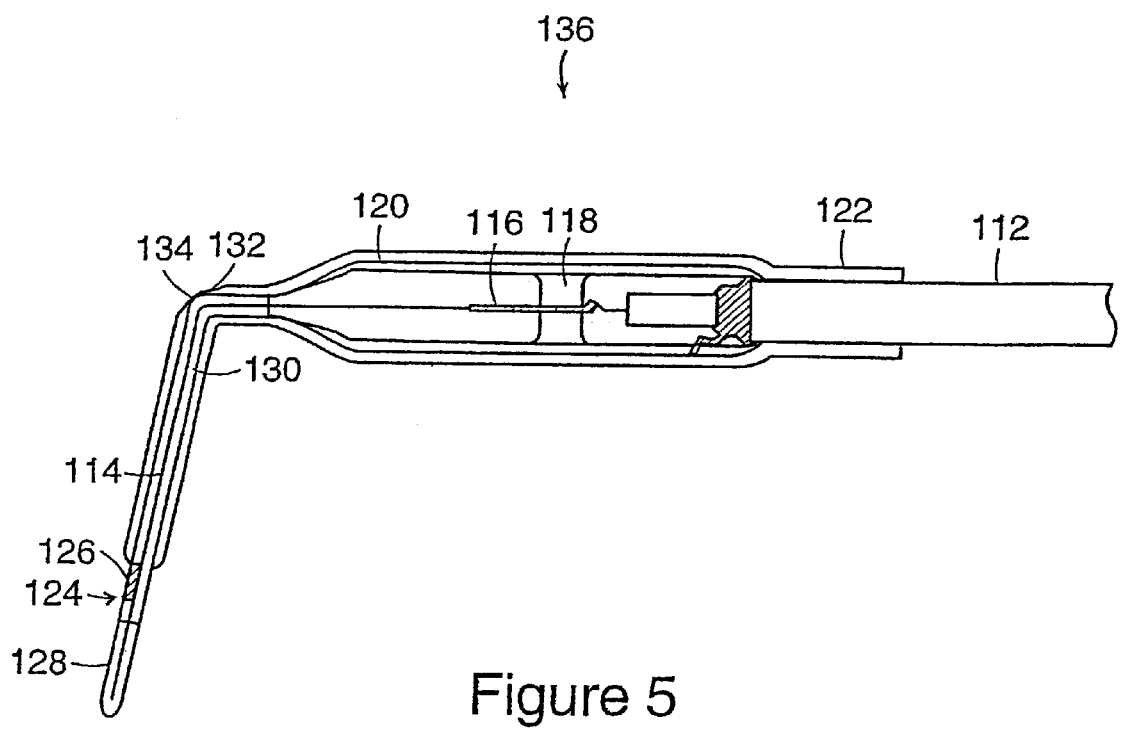
FIG. 5 illustrates a sectional view of an embodiment of a pH electrode.

FIG. 5 illustrates an embodiment of a pH electrode 136 used to monitor tissue acidosis. The electrode 110 can have a cable 112 connected to a silver wire 114. In a preferred embodiment, the silver wire 114 is an Ag/AgCl (silver/silver chloride) wire. In another preferred embodiment, the cable 112 is connected to the silver wire 114 by a platinum wire 116 passing through a glass seal 118. The cable 112 and wires 114, 116 are encased in a housing 120 which is encased in shrink tubing 122. The electrode 110 has a glass stem 124 which houses the silver wire 114, a thermistor 126, a pH sensor 128, and a gelled electrolyte 130. The electrode 110 can also have a suture groove 132 to allow the electrode 110 to be secured to the site where it is used. The electrode 110 can also have a bendable joint 134 which allows the user to adjust the positioning of the electrode 110 prior to or during use. The glass stem 124 is pointed to allow direct insertion into tissues. In a preferred embodiment, the glass stem 124 is made of lead glass. The electrode can be sterilized by ethylene oxide or gamma irradiation. A pH electrode suitable for use with the invention is available from Vascular Technology Inc., 175 Cabot Street, Lowell, Mass. This particular electrode can be inserted into tissue to a depth of up to 10 mm, has a diameter of 1 mm, and employs a pH sensor in the distal 4 mm of the probe.

Tissue pH is an important clinical measurement. Local acidosis, which can be measured as a distinct drop in pH, has been associated with ischemia. Temperature is preferably measured simultaneously with the pH to allow for the calibration and temperature correction of the tissue pH measurement. Temperature correction of the pH is important, particularly in procedures, such as open-heart surgery, which require significant cooling. The pH electrode uses combination pH/temperature sensors, each of which contains a temperature-sensing element mounted inside the pH-sensing sensor.

Glass pH electrodes are the method most commonly used to obtain accurate clinical pH measurements. They consist of a hollow glass sensor filled with electrolyte that is in turn in contact with an internal reference wire. Due to the nature of the glass used, an electric potential is developed across the glass. This potential is proportional to the difference between the pH of the analyte solution in contact with the exterior surface of the glass and the essentially constant pH of the internal buffer solution.

In order to make an electrical measurement, a complete electric circuit must be formed. Therefore, a second electrical contact with the analyte solution must be made. This is accomplished through the use of a needle reference electrode. It consists of a silver chloride needle in contact with a constant molarity salt solution. The salt solution is placed in contact with the analyte solution, i.e., the patient's tissue, using suitable isolation mechanism, in this case through the use of gelled salt solution that has been placed in a flexible tube, the open end of which is placed in contact with the patient.

The Nernst equation predicts that under constant environmental conditions, the output of the glass pH electrode is linear with pH. Therefore, the electrical output of the sensor can be converted to pH by the use of a simple straight-line curve-fit. This will require determining the electrical output of the electrode at two different pH values, from which the slope and offset constants for the straight-line equation can be calculated. The commonly available standards buffers for pH electrode calibration have pH values of 4, 7, and 10. The 4 and 7 buffers have been chosen for use with this system. The 7-pH buffer was chosen because the electrode's zero-potential point is near pH 7. The 4-buffer was chosen because pH values of the greatest interest lie somewhat below pH 7.

The theoretical sensitivity-the slope-of this type of electrode is 59.16 mV/pH at 25° C. For real electrodes, it tends to be a little less, the value being slightly different from one electrode to another and, for a given electrode, varying over its useful life.

The zero potential point is defined, as that analyte pH value for which the measured output voltage is zero, after correcting for any difference in the salt concentrations of the internal and reference solutions. The zero potential point should occur, therefore, when the analyte pH value is the same as the pH value of the pH sensor's internal buffer. If a measurement is actually made under these conditions, however, a non-zero potential will, in general, be measured. This occurs when the CI connection that the sensor's internal reference wire is exposed to differs from the concentration that the reference needle is exposed to, or if both reference wires are not made of the same material. In this system, the reference needle is immersed in a saturated KCl gel, while the sensor's internal reference wire is exposed to an 0.87 M concentration of KCl in the internal buffer. This difference results in a measured potential of about +30 mV at 25° C. when the analyte has the same pH value as that of the internal buffers, nominally 6.33 pH at 25° C. Thus, in order to measure the true zero potential point, it is necessary to correct the measured voltage by subtracting 30 mV from it. The pH 7 buffer is used during calibration for zero point calibration and is the closest readily available buffer value to 6.33.

Since there is some variation in output from the ideal values as just described, both from sensor to sensor and over extended periods of time for the same sensor, the pH sensors must be calibrated prior to each use. This is accomplished automatically during the calibration procedure by placing the sensors first in the slope buffer (4.00 pH) and then in the zero potential point buffer (7.00 pH). The microprocessor reads the output of the sensors in mV, correcting for the salt differential, determines when the readings are stable and then computes the slope and offset calibration factors for each sensor. Both the slope and zero potential point vary with temperature and are corrected for by the monitor's software.

The pH electrode's combination pH/temperature sensor uses a precision thermistor element to measure temperature. The thermistor is one of the most common temperature measuring devices in use. It consists of a small bead of metallic oxide semiconducting ceramic. The material's electrical resistance varies inversely with temperature in a non-linear manner.

To measure temperature, the thermistor is electrically placed in series with a fixed resistor in the monitor that has precisely known resistance. A voltage is applied across the series combination and the voltage at the junction of the thermistor and resistor is measured. This measured value, in conjunction with the known values of the fixed resistor and of the applied voltage, is used to calculate the resistance of the thermistor. The temperature is then determined by means of a look-up table stored in the microprocessor program. The thermistor sensors used with this system are manufactured to a level of precision that makes individual calibration by the user of the system unnecessary.

While the pH electrodes and monitoring system have been described for use in determining the ischemia of cardiac tissue, the pH system and methods can be used in other types tissue as well. The pH system can be used to monitor rejection in organ transplantation, to assess mesenteric ischemia, to monitor and assess brain blood flow and to monitor flaps in plastic surgery.

What is claimed is:

1. A method of detecting acidosis in tissue comprising the steps of:
    contacting tissue of a patient with a pH electrode;
    measuring the pH of the tissue with the pH electrode to monitor the pH of the tissue during cardiac surgery;
    determining if the tissue pH falls below a threshold level indicative of acidosis;
    selecting a site from a plurality of sites for delivery of a preservation solution based on the monitoring of the pH of the tissue; and
    delivering the preservation solution to the site to raise the pH of the tissue if the tissue pH measurement falls below the threshold level indicative of acidosis.

2. The method of detecting acidosis of claim 1 wherein the step of contacting a pH electrode further comprises inserting the pH electrode into the tissue.

3. The method of detecting acidosis of claim 1 wherein the step of delivering the preservation solution further comprises the step of delivering the preservation solution to a heart at a plurality of said sites.

4. The method of detecting acidosis of claim 1 wherein the step of delivering the preservation solution to a heart further comprises the step of altering the flow rate of the preservation solution.

5. The method of detecting acidosis of claim 1 wherein the step of delivering the preservation solution to a heart further comprises the step of altering the temperature of the preservation solution.

6. The method of detecting acidosis of claim 1 wherein the step of delivering the preservation solution to a heart further comprises the step of altering the site of delivery of the preservation solution.

7. The method of detecting acidosis of claim 1 wherein the step of delivering the preservation solution to a heart further comprises the step of repositioning a tip of a catheter which delivers the solution.

8. The method of detecting acidosis of claim 1 wherein the step of delivering the preservation solution to a heart further comprises the step of directing the solution through a manifold.

9. The method of detecting acidosis of claim 1 wherein the step of delivering the preservation solution to a heart further comprises the step of applying direct coronary artery pressure on a proximal portion of the artery.

10. The method of detecting acidosis of claim 1 wherein the step of delivering the preservation solution to a heart further comprises the step of occluding an orifice of a left main coronary artery.

11. The method of detecting acidosis of claim 10 wherein the step of occluding an orifice of a left main coronary artery is performed using a balloon catheter.

12. The method of detecting acidosis of claim 1 wherein the step of delivering the preservation solution to a heart further comprises the step of inflating a balloon of a retrograde coronary sinus catheter.

13. The method of detecting acidosis of claim 1 wherein the step of delivering the preservation solution to a heart further comprises the step of administering a bolus of preservation solution through an orifice of a right coronary artery.

14. The method of detecting acidosis of claim 1 wherein the step of contacting a pH electrode to the tissue of a patient is performed manually.

15. The method of detecting acidosis of claim 1 wherein the step of contacting a pH electrode to the tissue of a patient is performed by a percutaneous catheter.

16. The method of detecting acidosis of claim 1 wherein the step of contacting a pH electrode to the tissue of a patient is performed using a laparoscope.

17. The method of detecting acidosis of claim 1 wherein the step of contacting a pH electrode to the tissue of a patient is performed using an endoscope.

18. The method of detecting acidosis of claim 1 wherein the step of contacting a pH electrode to the tissue of a patient is performed using a colonscope.

19. A method for correcting acidosis at a site of interest in myocardial tissue comprising the steps of:

contacting a site of interest in myocardial tissue of a patient with a pH electrode and a temperature sensor during cardiac surgery;

measuring the pH and the temperature of the site of interest;

determining a temperature correction of the pH measurement to provide a corrected pH measurement;

determining if the pH of the site of interest falls below a threshold level indicative of acidosis using the corrected pH measurement;

selecting a site from a plurality of sites for delivery of a preservation solution based on the measured pH of the tissue; and delivering a preservation solution to a heart to raise the pH of the site of interest in the myocardial tissue if the corrected pH measurement falls below the threshold level indicative of acidosis.

20. The method for correcting acidosis of claim 19 wherein the pH of the site of interest in the myocardial tissue is raised more than 0.1 pH unit.

21. The method for correcting acidosis of claim 19 wherein the step of delivering the preservation solution to a heart further comprises the step of varying the flow rate of the preservation solution.

22. The method for correcting acidosis of claim 19 wherein the step of delivering the preservation solution to a heart further comprises the step of varying the temperature of the preservation solution.

23. The method for correcting acidosis of claim 19 wherein the step of delivering the preservation solution to a heart further comprises the step of varying the site of delivery of the preservation solution.

24. The method for correcting acidosis of claim 19 wherein the step of delivering the preservation solution to a heart further comprises the step of repositioning the tip of the catheter which delivers the solution.

25. The method for correcting acidosis of claim 19 wherein the step of delivering the preservation solution to a heart further comprises the step of applying direct coronary artery pressure on a proximal portion of the artery.

26. The method for correcting acidosis of claim 19 wherein the step of delivering the preservation solution to a heart further comprises the step of occluding an orifice of a left main coronary artery.

27. The method for correcting acidosis of claim 26 wherein the step of occluding an orifice of a left main coronary artery is performed using a balloon catheter.

28. The method for correcting acidosis of claim 19 wherein the step of delivering the preservation solution to a heart further comprises the step of inflating a balloon of a retrograde coronary sinus catheter.

29. The method for correcting acidosis of claim 19 wherein the step of delivering the preservation solution to a heart further comprises the step of administering a bolus of preservation solution through an orifice of a right coronary artery.

30. The method for correcting acidosis of claim 19 further comprising the step of assessing the adequacy of coronary revascularization following a heart surgery procedure.

31. The method for correcting acidosis of claim 19 further comprising the step of identifying viable but nonfunctioning heart muscle.

32. The method for correcting acidosis of claim 19 further comprising the step of monitoring the pH of the heart muscle post-operatively.

* * * * *